US012698312B2

(12) United States Patent
Borsello et al.

(10) Patent No.: US 12,698,312 B2
(45) Date of Patent: Aug. 4, 2026

(54) JNK3 INHIBITORY PEPTIDES

(71) Applicants: UNIVERSITA' DEGLI STUDI DI MILANO, Milan (IT); UNIVERSITA' DEGLI STUDI DI ROMA "TOR VERGATA", Rome (IT); UNIVERSITA' POLITECNICA DELLE MARCHE, Ancona (IT)

(72) Inventors: Tiziana Borsello, Milan (IT); Mattia Falconi, Rome (IT); Daniele Di Marino, Ancona (IT)

(73) Assignees: UNIVERSITA' DEGLI STUDI DI MILANO, Milan (IT); UNIVERSITA' DEGLI STUDI DI ROMA "TOR VERGATA", Rome (IT); UNIVERSITA' POLITECNICA DELLE MARCHE, Ancona (IT)

( * ) Notice: Subject to any disclaimer, the term of this patent is extended or adjusted under 35 U.S.C. 154(b) by 876 days.

(21) Appl. No.: 17/998,411

(22) PCT Filed: May 14, 2021

(86) PCT No.: PCT/IB2021/054144
§ 371 (c)(1),
(2) Date: Nov. 10, 2022

(87) PCT Pub. No.: WO2021/229521
PCT Pub. Date: Nov. 18, 2021

(65) Prior Publication Data
US 2023/0192785 A1    Jun. 22, 2023

(30) Foreign Application Priority Data
May 15, 2020    (IT) ........................ 102020000011176

(51) Int. Cl.
*C07K 14/47*    (2006.01)
*A61K 47/64*    (2017.01)
*A61P 25/28*    (2006.01)

(52) U.S. Cl.
CPC ........ *C07K 14/4702* (2013.01); *A61K 47/645* (2017.08); *A61P 25/28* (2018.01); *C12Y 207/11024* (2013.01)

(58) Field of Classification Search
None
See application file for complete search history.

(56) References Cited

FOREIGN PATENT DOCUMENTS

| | | |
|---|---|---|
| EP | 1 491 213 A1 | 12/2004 |
| EP | 1 928 903 B1 | 5/2012 |

OTHER PUBLICATIONS

Cleveland Clinic (downloaded from URL :<Neurodegenerative Diseases: What They Are & Types (clevelandclinic.org)>) (Year: 2025 ).*
Aster Mental Health (downloaded from URL :<https://www.astermentalhealth.com/attention-deficit-hyperactivity-disorder-adhd/) (Year: 2025).*
International Search Report issued Aug. 19, 2021 in PCT/IB2021/054144, 3 pages.
Lattin, J. E., et al., "Beta-arrestin 2 is required for complement C1q expression in macrophages and constrains factor-independent survival", Molecular Immunology, Pergamon, GB, vol. 47, No. 2-3, XP026886953, pp. 340-347.
Antoniou, X., et al., "JNK3 as a Therapeutic Target for Neurodegenerative Diseases", 2011, Journal of Alzheimer's Disease, vol. 24, 2011, XP055763883, pp. 633-642.
Long, J., et al., "JNK3 involvement in nerve cell apoptosis and neurofunctional recovery after traumatic brain injury" Jun. 6, 2013 (Jun. 6, 2013), vol. 8, No. 16, pp. 1491-1499.
Anonymous, "Annual Report 2012", Alzheimer's Association, Retrieved from the internet. URL:/https://www.yumpu.com/en/document/view/16063373/untitled-istituto-do-ricerche-farmacologiche-mario-negrl [retrieved on Jan. 12, 2021]. p. 133, May 1, 2013 (May 1, 2013). XP056764073. 24 pages.
Pirianov, G., et al. "Deletion of the c-Jun N-terminal kinase 3 gene protects neonatal mice against cerebral hypoxio-ischaemic injury", 2007 Journal of Cerebral Blood Flow & Metab., 27, pp. 1022-1032.
Brecht, S. et al, "Specific pathophysiological functions of JNK isoforms in the brain", 2005, Eur J Neurosci , 21, pp. 363-377.
Kimberly, W.T., et al., "Physiological Regulation of the β-Amyloid Precursor Protein Signaling Domain by c-Jun N-Terminal Kinase JNK3 during Neuronal Differentiation", 2005, in J Neurosci 25, pp. 5533-5543.
Kuan, C.Y., et al, "A critical role of neural-specific JNK3 for ischemic apoptosis" 2003, Proc Natl Acad Sci., USA 100, pp. 15184-15189.
Miller, W.E. et al, "Identification of a Motif in the Carboxyl Terminus of b-Arrestin2 Responsible for Activation of JNK3", Jul. 27, 2001, in J Biol Chem 276, pp. 27770-27777.
Guo, C., et al., "The β-Arrestin-2 Scaffold Protein Promotes c-Jun N-terminal Kinase-3 Activation by Binding to Its Nonconservad N Terminus", 2006, in J Biol Chem, 283, pp. 15903-15911.
Rajan. R.K.. et al., "Identification and neuroprotective evaluation of a potential c-Jun N-terminal kinase 3 inhibitor through structure-based virtual screening and in-vitro assay", 2020, J Computer-Aided Mol Des. doi.org/10.1007/s10822-020-00297-y, pp. 671-682.
Oh, Y., et al., "Discovery of 3-alkyl-5-aryl-1-pyrimidyf-1H-pyrazole derivatives as a novel selective inhibitor scaffold of JNK3" 2020, J Enz Inhib Med Chem., 35, pp. 372-376.
(Continued)

*Primary Examiner* — Sergio Coffa
(74) *Attorney, Agent, or Firm* — Oblon, McClelland, Maier & Neustadt, L.L.P.

(57) ABSTRACT

The subject of the present invention is a peptide, natural or synthetic, which comprises an amino acid sequence that has at least 80% sequence identity with the sequence SDRSLHLEANEKGENVNVHVTKTRADK-SKIKVSVRQYADINEKGEAQYKCPVAQLE (SEQ ID NO: 1). A further object of the present invention is said peptide which has at least 80% sequence identity with the sequence SEQ ID NO: 1 which is a JNK3 inhibitor for use in the prevention and/or treatment of neurodegenerative or neurodevelopmental diseases.

10 Claims, 10 Drawing Sheets

Specification includes a Sequence Listing.

(56) References Cited

OTHER PUBLICATIONS

Pan. J., et al., "Small Peptide Inhibitor of JNK3 Protects Dopaminergic Neurons from MPTP Induced Injury via Inhibiting the ASK1-JNK3 Signaling Pathway", 2015 in PloS ONE 10 (4): e0119204.doi: 10.1371 / journal.pone.0119204, pp. 1-16.

Sclip, A., et al., "c-Jun N-terminal Kinase Regulates Soluble Aβ Oligomers and Cognitive Impairment in AD Mouse Model", 2011 in J Biol Chem. 286, pp. 43871-43880.

Needleman, S.B., et al., "A General Method Applicable to the Search for Similarities in the Amino Acid Sequence of Two Proteins", 1970, J Mol Biol., 48, pp. 443-453.

Smith. T.F., et al., "Identification of Common Molecular Subsequences", 1981, J Mol Biol., 147, pp. 195-197.

Makabe, K., et al., "Atomic structures of peptide self-assembly mimics", 2006, Proc Natl Acad Sci USA. 103, pp. 17753-17758.

Sclip, A et al, c-Jun N-terminal kinase has a key role in Alzheimer disease synaptic dysfunction in vivo, 2014 Cell Death Dis. 5: e1019: pp. 1-9.

D'Amelio, M., et al., "Caspase-3 triggers early synaptic dysfunction in a mouse model of Alzheimer's disease", 2011 Nature Neuroscience 14, pp. 69-76.

Sclip, A., et al., "Soluble Aβ oligomer-induced synaptopathy: c-Jun N-terminal kinase's role", 2013 Journal of Molecular Cell Biology 5, Issue 4, pp. 277-279.

* cited by examiner

SDRSLHLEANEKGENVNVHVTKTRADKSKIKVSVRQYADINEKGE
AQYKCPVAQLE (SEQ ID NO: 1)

SDRSLHLEAEKGNVNVHVTKTEKGKIKVSVRQYADIEKGAQYKCP
VAQLE (SEQ ID NO: 2)

SDRSLHLEAEKGNVNVHVTKTADKKIKVSVRQYADIEKGAQYKCP
VAQLE (SEQ ID NO: 3)

SDRSLHLEANEKGENVNVHVTKTNEKGEKIKVSVRQYADINEKGE
AQYKCPVAQLE (SEQ ID NO: 4)

JNK3 INHIBITORY PEPTIDES

The present invention refers to selective and specific peptides JNK3 MAP kinase inhibitors in the central nervous system and to their use in the treatment of acute and/or chronic diseases of the central nervous system (CNS), as well as in neurodevelopmental disorders.

BACKGROUND

Neurodegenerative diseases represent an emerging health problem in the Western world, particularly with the aging of the population. Therapies for this type of pathology are still rare and in most cases not decisive.

Synaptic dysfunction, or synaptopathy, is a term used to define the key features of neurodegenerative and psychiatric disorders. Many CNS diseases, including Alzheimer's disease (AD), prion diseases. Huntington's disease, Parkinson's disease, schizophrenia, autism, ataxia, fragile-X syndrome and depression are characterized by dysfunction of excitatory synapses. Currently, the most studied synaptopathy is the one characterizing AD; it is strongly correlated to cognitive decline and develops during the early stages of the disease, as it is already found in patients with a mild cognitive deficit. Since synapse dysfunction precedes neuronal death and surviving neurons possess remarkable synaptic repair and functional recovery capacity, therapeutic intervention aimed at protecting synapses from dysfunction is a goal to improve neurological functions in several neurodegenerative diseases. To date, there is no treatment available to prevent synaptopathy.

c-Jun N-terminal Kinase (JNK) is a MAP kinase expressed in three different isoforms, JNK1, JNK2 and JNK3. Isoform 3 is specific to the central nervous system (Antoniou X. et al., 2011 J Alzheimer's Dis. 24:633-42). In mouse hippocampal neurons, deletion of the JNK3 gene caused resistance to apoptosis, to glutamate receptor agonist kainic acid induced excitotoxicity, and also to MPTP-induced death (Pirianov G. et al., 2007 J Cereb Blood Flow Metab 27:1022-1032; Brecht S. et al., 2005 Eur J Neurosci 21:363-377). Kimberly W. T. et al., 2005 in J Neurosci 25:5533-5543 demonstrate that JNK3 is the main kinase responsible for APP phosphorylation at residue T668 (P-APP) during neuronal differentiation.

In nervous tissue, JNK signalling is 16 times more active than in all other tissues (Kuan C. Y. et al., 2003 Proc Natl Acad Sci USA 100:15184). In particular, JNK3 is the most responsive isoform to stress signals and the activation of JNK3 has been linked to multiple neurodegenerative diseases.

The β-arrestin-2 protein is able to specifically bind JNK3 only and not JNK1 and JNK2, the other isoforms of the JNK family. Miller W. E. et al., 2001 in J Biol Chem. 276:27770-7, demonstrate that the β-arrestin-2 region important for interaction with JNK3 is found in the C-terminal region of the protein, where amino acids 186 to 410 are arranged to form a tertiary-shaped structure antiparallel β barrel formed by eight β-filaments. In particular, the amino acids 196 to 201 (Asp196, Arg197, Ser198, Leu199, His200, Leu201) are very similar to the conserved binding motif present in many proteins that bind JNK kinases, called domain D.

Guo C., Whitmarsh A. J., 2008 in J Biol Chem. 283: 15903-11 mapped JNK3 residues essential for binding to β-arrestin-2. These correspond to amino acids 9 to 18 (Cys9, Ser10, Glu11, Pro12, Thr13, Leu14, Asp15, Val16, Lys17, Ile18) of the non-conserved N-terminal domain of JNK3, demonstrating that JNK3 does not bind directly to the presumed D domain of β-arrestin-2, but to the C-terminal region (amino acids 228 to 410), where residues within the D domain determine the specificity of the β-arrestin-2-JNK3 bond and in particular indicate the importance of Ser198 in β-arrestin-2.

Rajan R. K. and Ramanathan M., 2020 in J Computer-Aided Mol Des. doi.org/10.1007/s10822-020-00297-y describe small molecule inhibitors of JNK3. One of the compounds identified was shown to be active in a cell-free JNK3 kinase assay and in an in vitro neuro protection assay.

Small molecules are also described by Oh Y. et al., 2020 in J Enz Inhib Med Chem. 35:372-376. In silico data show a selectivity of a selection of these towards JNK3.

Pan J. et al., 2015 in PloS ONE 10 (4): e0119204.doi: 10.1371/journal.pone.0119204, describe a 21 amino acid fusion peptide, named JNK3-N-Tat, which has been shown to inhibit the activation of JNK3 in a cellular model of Parkinson's disease, showing protective effects against MPTP-induced dopaminergic neuronal toxicity.

EP1928903B1 describes a peptide, D-JNKI1, a non-selective inhibitor of the three isoforms of JNK.

Sclip A. et al., 2011 in J Biol Chem. 286:43871-43880, describe the results obtained in a chronic treatment with the same peptide D-JNKI1, permeable to CPP cells, in an in vivo model of AD (TgCRND8 mice), showing that the inhibition of all the isoforms of JNK, following chronic treatment with D-JNKI1, promotes the recovery of impaired LTP (Long Term Potentiation) and behavioural memory in the TgCRND8 mouse model.

EP1491213A1 describes a c-Jun inhibitory peptide, the main target of JNK which, when phosphorylated, leads to neuronal death.

There is a strong need to have specific and selective inhibitors of JNK3 that can be used in the prevention and treatment of neurodegenerative or neurodevelopmental diseases.

DESCRIPTION

The subject of the present invention are peptides, natural or synthetic, specific inhibitors of JNK3. A further embodiment of the present invention is at least one peptide, natural or synthetic, specific inhibitor of JNK3, for use in the prevention and treatment of neurodegenerative diseases.

Figures 1, 2:
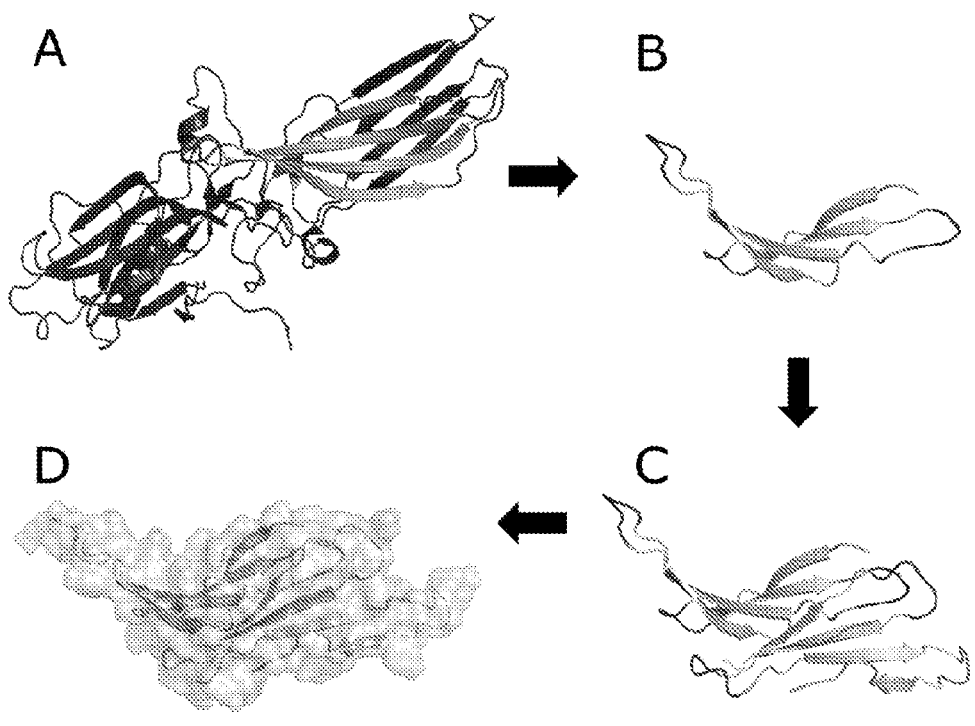
FIG. 1: Schematic representation of the extraction of the β-sheet from human β-arrestin-2. A) Complete structure of the β-arrestin-2 represented with a ribbon that follows the trend of the polypeptide chain. The gray ribbon, visible on the right side of the protein, indicates the portion of the β-sheet that has been extracted from the protein. B) The gray ribbon indicates the β-sheet, formed by 4 β-filaments, extracted from the structure of the β-arrestin-2, while the darker filament, between one B segment and the other, indicates the chain inversions used in the structure of the OspA protein of *Borrelia burgdorferi* (PDB ID: 2AF5). C) mini-β-arrestin-2 in dimeric structure. The β-sheet is shown by the gray ribbon while the chain reversals used by the OspA protein of *Borrelia burgdorferi* are shown by the dark filaments. D) Molecular surface of the mini-β-arrestin-2 in dimeric structure shown as a gray ribbon inside.
FIG. 2: Single-letter coded amino acid sequences of the extracted peptide SEQ ID NO: 1 (SIMBA2 long B) also called SIMBA2, as well as the additional peptides SEQ ID NO: 2 (SIMBA2 short A), SEQ ID NO: 3 (SIMBA2 short B), SEQ ID NO: 4 (SIMBA2 long A). The bold black sequence parts indicate the chain reversals used by the OspA protein structure from *Borrelia burgdorferi*, the remaining gray sequence parts indicate the β-strands extracted from the human β-arrestin-2 model.

The peptides according to the present invention are designed on the interaction domain between JNK3 and β-arrestin-2. The inhibition effect observed with the peptides according to the present invention is a competitive substrate effect, obtained by introducing an excess of the β-arrestin-2 domain and sequestering JNK3 which will bind to the peptide instead of β-arrestin-2, preventing thus the activity of JNK3 on its physiological targets and disrupting the chain of events leading to cell death.

In one embodiment, the object of the present invention is a peptide, natural or synthetic, which comprises an amino acid sequence that has at least 80% sequence identity with the SEQ ID NO: 1, identity calculated using a pairwise sequence alignment method, such as EMBOSS needle: Needleman S B and Wunsch C. D., 1970 J Mol Biol. 48:443-53 or EMBOSS water: Smith T. F. and Waterman M. S., 1981 J Mol Biol. 1471:195-7.

In one embodiment, said peptide is conjugated to a polypeptide transport moiety, for example rich in basic amino acids, such as arginine, lysine, histidine, asparagine, glutamine. Said moiety is bound to said peptide and is capable or has the ability to facilitate the absorption of said active in a mammalian tissue or cell (for example human or animal). Said polypeptide transport moiety is selected, for example, in the group comprising an HIV transport subdomain (for example, HIV-1) Protein Tat, a homeoprotein transport sequence, a histidine tag (of length between 4 and 30 repetitions of histidine) or pharmaceutically acceptable derivatives thereof. By way of example, said polypeptide transport portion is selected from the group consisting of TAT protein, an Antennapedia homeodomain, or other sequences known to the skilled in the art for its ability to permeabilize the lipid bilayer, so as to allow the peptide to enter. in cells and in the central nervous system.

In a preferred form, said peptide is conjugated to the TAT protein, where said TAT protein is synthesized in amino acids D (SEQ ID. NO: 5). The authors of the present invention have in fact demonstrated that the TAT protein synthesized in amino acids D improves the stability of the peptide. Said TAT protein to which the peptide according to the present invention is conjugated in a preferred embodiment has the SEQ ID NO: 5=YGRKKRRQRRR.

In a preferred embodiment, said peptide has at least 85% sequence identity with SEQ ID NO: 1. In a further embodiment, it has at least 90% sequence identity with SEQ ID NO: 1. In a further embodiment, it has at least 95% sequence identity with SEQ ID NO: 1.

In a further embodiment, the peptide comprises the SEQ ID NO: 1.

Said variants, or any other conceivable reduced form of the peptide SEQ ID NO: 1, consist of any possible subsequence of SEQ ID NO: 1, or of any possible substituent thereof.

In a preferred embodiment, said substituents replace each amino acid with another amino acid having comparable chemical-physical characteristics.

In one embodiment, said amino acids are natural amino acids, or L amino acids. In a further embodiment, they are D amino acids.

In one embodiment, the peptide consists of SEQ ID NO: 1.

In one embodiment, the peptide consists of the SEQ ID NO: 1 with amino acids synthesized in L, conjugated to the TAT protein with the amino acids synthesized in D (SEQ ID NO: 5).

In a further embodiment, the peptide consists of SEQ ID NO. 2, or in SEQ ID NO: 3, or in SEQ ID NO 4.

The peptides according to the present invention have been surprisingly able, in cell-free studies, in vitro and in vivo, to specifically and selectively inhibit the isoform 3 of JNK, without interfering with the isoforms JNK1 and JNK2.

The same peptides have surprisingly demonstrated neuroprotective activity in pathological situations.

Said peptides have been shown to be active in chronic and/or acute pathologies.

By way of example, the authors of the present invention have demonstrated the activity of said peptides against the toxicity of synapto-toxic Aβ fragments both in vitro and in vivo, in two different animal models. In particular, in vivo experiments were conducted in a validated mouse model of AD, the transgenic mouse TgCRND8. The animal, which overexpresses a mutated form of the amyloid precursor protein, was acutely treated with at least one peptide according to the present invention. The experiments have shown how the specific inhibition of JNK3 obtained with the peptides according to the present invention reduces the phosphorylation of APP and Tau, the two main markers of AD.

In the same animal model, a neuro protective effect against synaptic dysfunction was also observed with the peptides according to the present invention. On the other hand, synaptic dysfunction, characterised by alterations in the protein levels of the markers found in the PSD region, observed in AD animals and not in control animals, is not present in AD animals treated with the peptides according to the present invention. The data obtained show that the treatment stabilizes the levels of PSD95, an active protein in the post-synaptic element, and of the NMDA and AMPA receptors of the excitatory synapse.

In vivo experiments were also performed on a second mouse model, the Tg5xFAD mouse, which has as many as 5 mutations (3 on APP and 2 on PS1), AD model that presents very severe symptoms. Also in this animal model, the efficacy of the peptides according to the present invention has been confirmed.

Said peptides were also tested in acute, in an animal model of TBI (Traumatic Brain Injury). The observed data show the efficacy of an acute treatment with the peptides according to the present invention which, administered in acute form after the traumatic event, have been shown to be able to prevent the activation of the JNK3 signalling pathway following the trauma.

The peptides according to the present invention did not lead to the onset in vivo of major side effects.

The peptides according to the present invention are therefore particularly effective for use in the treatment of both acute pathologies of the nervous system, such as ischemia and head trauma, and chronic such as Alzheimer's, Parkinson and Huntington's diseases, frontotemporal dementia. Down syndrome, schizophrenia and psychiatric pathologies, spino-cerebellar ataxia, muscular atrophy, amyotrophic lateral sclerosis, progressive supranuclear palsy, corticobasal degeneration, Pick's disease, prion diseases. The peptides according to the present invention are also employed for use in the treatment of pathologies of the development of the nervous system, such as, by way of example, the Rett and Angelman syndromes, and in general the spectrum of autism.

These peptides are advantageously applied in the treatment of diseases involving inflammation of the brain parenchyma, glaucoma and maculopathy, diabetes and diabetic retinopathies, in the treatment of deafness and damage to the inner ear hair cells.

Advantageously, the peptides according to the present invention allow to intervene early in the neurodegenerative process, impacting an upstream event, i.e. synaptic dysfunction, the first toxic event in diseases of the central nervous system. Furthermore, the peptides according to the present invention have been shown to be able to selectively and specifically reach a completely new target, namely JNK3, in the CNS. The inhibition of JNK3 obtained with the peptides object of the present invention is based on their unique ability to interfere with the specific protein-protein interaction between JNK3 and β-arrestin-2, thus reaching high specificity levels. The specific inhibition of JNK3 allows to act on the JNK which is expressed only in the Central Nervous System, preventing its activation in response to stress signals and therefore of pathological reaction.

The following examples have the sole purpose of providing experimental evidence of obtaining and of the advantages related to some embodiments of the present invention. They are not to be read in any way as limiting the scope of the invention, whose scope of protection is defined by the claims.

EXAMPLE 1: IN SILICO DESIGN OF THE PEPTIDE

A homology model was created which allowed to delineate the structural and functional properties of the protein interfaces through which the recognition between JNK3 and β-arrestin-2 takes place.

The sequence and/or the interaction surface of β-arrestin-2 that specifically binds JNK3 has been minimized in order to create a mini-β-arrestin-2. The reduction was operated in such a way that the reduced sequence maintained the ability to fold in the same conformation observed in the complete enzyme structure, thus ensuring a very similar surface for interaction with JNK3.

The C-terminal region of β-arrestin-2 is represented by an antiparallel β barrel formed by 8 β-filaments (FIG. 1A, portion on the right in gray). The interaction with JNK3 is mainly due to 4 antiparallel β-filaments (ribbons in gray in FIG. 1A) accessible to the solvent that form a single distorted β-sheet which gives rise to a concave interaction surface. The β-sheet is able to recognize the unstructured N-terminal tail of JNK3 which, when located in proximity to the β-arrestin-2, probably assumes a helical conformation that is particularly suitable for interacting with a concave β-sheet. The concave surface formed by 4 β-filaments was extracted from the complete model structure of the human β-arrestin-2 and the original topology was recreated in order to generate a single β-sheet formed by contiguous β-filaments capable of folding independently.

The folding strategy used by the outer surface protein of *Borrelia burgdorferi* OspA has been adopted in which the single β-leaflet, which lies between two globular domains, is composed of two β-hairpin units and can be considered as an excellent prototype of units for self-assembly.

Therefore, the chain reversals were introduced using the 5 residues that make up the chain reversals observed in the central, single-layered β-sheet of *Borrelia burgdorferi*'s OspA outer surface protein (PDB ID: 2AF5) (Makabe et al., 2006 Proc Natl Acad Sci USA. 103:17753-17758) (FIG. 2B, darker filaments).

The number of amino acid residues in the designed β-sheet is 56, a length that experimentally allows to obtain the protein through direct synthesis methods or through recombinant DNA methods.

Furthermore, to obtain a completely soluble protein, the N and C-terminal regions of the β-sheet have been designed in order to prevent an uncontrolled aggregation of multiple peptides which could be very harmful to the cell (Makabe et al., 2006, cit.).

Using this strategy, the self-assembling β-sheet peptide was constructed while maintaining, at the same time, the β-sheet geometry observed in the complete β-arrestin-2 structure and the complete recognition site that ensures the interaction β-arrestin-2-JNK3.

The name assigned to this peptide is SIMBA2 (Synthetic Interfering Mini Beta-Arrestin-2) and has the following amino acid sequence:

```
                                        (SEQ ID NO: 1)
SDRSLHLEANEKGENVNVHVTKTRADKSKIKVSVRQYADINEKGEAQYK
CPVAQLE.
```

With the same approach, further peptides have been described, having the following amino acid sequence:

```
                                        (SEQ ID NO: 2)
SDRSLHLEAEKGNVNVHVTKTEKGKIKVSVRQYADIEKGAQYKCPVAQL
E (SEQ ID NO: 3)
SDRSLHLEAEKGNVNVHVTKTADKKIKVSVRQYADIEKGAQYKCPVAQL
E (SEQ ID NO: 4)
SDRSLHLEANEKGENVNVHVTKTNEKGEKIKVSVRQYADINEKGEAQYK
CPVAQLE
```

The sequences are shown in FIG. 2 where the residues extracted from the human β-arrestin-2 model are highlighted in gray and the chain inversions used by the OspA protein structure from *Borrelia burgdorferi* are highlighted in black.

FIG. 1 schematises the peptide design procedure which comprises 5 steps:

1) use of the homology modelling procedure to generate a model of the structure of human β-arrestin-2 starting from the coordinates of bovine β-arrestin-2 (FIG. 1A);
2) the coordinates of a specific structural portion of the model, which through experimental investigation proved to interact with JNK3, were extracted from the human β-arrestin-2 model (FIG. 1B);
3) the β-filaments extracted from the human β-arrestin-2 model were reassembled, through the use of chain reversals that allow the formation of β-hairpins in the OspA protein of *Borrelia burgdorferi*, to generate a stable β-sheet consisting of 4 β-filaments (FIG. 1B);
4) starting from two of the β-sheets referred to in step 3), a mini β-arrestin-2 dimer was obtained with molecular modelling techniques. The assembled dimeric mini-protein, due to the amphipathic nature and the shape complementarity of the monomers, becomes water-soluble as a dimer (FIGS. 1C, D).
5) The SIMBA2 monomer and dimer were tested for stability using long simulations of classical molecular dynamics.

EXAMPLE 2: SIMBA2 ACTIVITY IN VITRO

To evaluate the specificity of the four peptides described above for JNK3, the Alpha Screen Kinase Assay was performed, following the experimental method described for the cell-free assays. Briefly, this AlphaScreen assay is used to measure the ability of the JNK kinase to phosphorylate its targets. The kinase reaction was performed under the following buffer conditions of the assay: 20 mM Tris/HCl (pH 7.4), 10 mM $MgCl_2$, 1 mM DTT, 100 μM $Na_3VO_4$ and 0.01% Tween-20. Compounds (final concentration 5 μg/mL, 1% DMSO) or the control vehicle (final concentration 1% DMSO) were diluted in the assay buffer and mixed with JNK kinase (final concentration 5 nM). After an incubation time of 15 minutes at room temperature, biotinylated substrate, 6 nM final and ATP, 1 μM final diluted in assay buffer were added, followed by incubation of the dishes for 2 hours at room temperature. After this incubation period, the streptavidin donor and acceptor beads coated with anti-phosphosubstrate protein A antibody were added, with a final concentration of each component of 20 μg/mL, diluted in the following buffer: 20 mM Tris/HCl (pH 7.4). 200 mM NaCl, 80 mM ethylenediamine tetraacetic acid (EDTA) and 0.3% bovine serum albumin (BSA). After an overnight incubation, the dosage was measured using the AlphaQuest reader.

Figure 3:
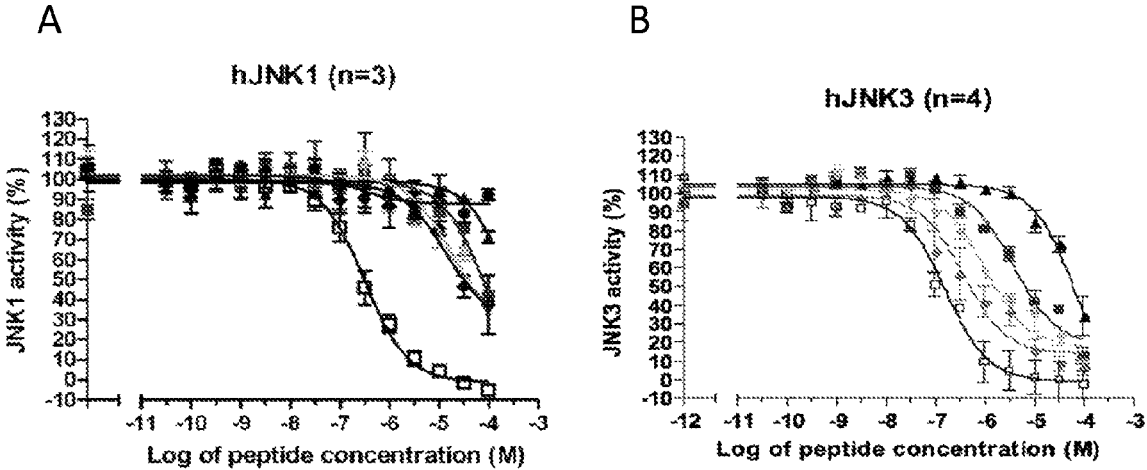
FIG. 3: A) Cell-free assay of JNK1 activity in the presence of peptides according to the invention. SIMBA2 short A (■), SIMBA2 long A (▲), SIMBA2 short B (gray triangle), SIMBA2 (diamond), SP600125 (□) was used as a positive control. B) JNK3 activity assay in the presence of the peptides according to the invention as indicated above, they inhibit the activity of JNK3 on p-c-Jun in a concentration-dependent manner, SP600125 (□) was used as a positive control.

The ATP-competitive and non-selective inhibitor SP600125 was used as a positive control for the different isoforms of JNK. As shown in FIG. 3B, the peptides according to the present invention have reached comparable levels of inhibition at the tested dosage conditions, indicating the inhibition of JNK3 activity in a cell-free assay in a dose-dependent manner.

The ability of the four peptides to inhibit the other JNK isoforms was then tested. In particular, we focused on JNK1 which, with JNK3, is the main isoform in the neurons and has about 91% homology and 95% similarity with JNK3, whereas JNK1 has only about 83% homology and 90% of similarity with JNK2. The peptides according to the present invention show no effect on the activity of JNK1 (FIG. 3A) whereas the expected activity was measured with SP600125 (FIG. 3A, □)

Figure 4:
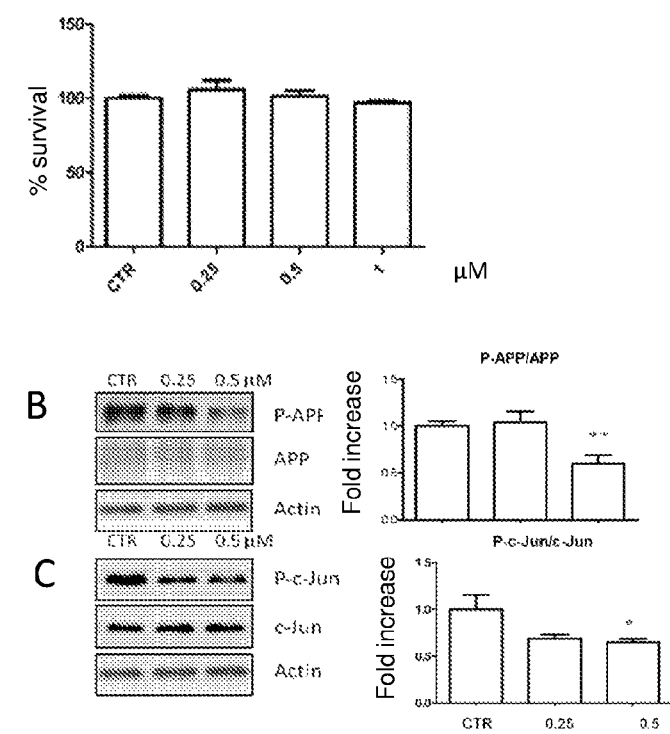
FIG. 4: A) Toxicity at the indicated concentrations of SIMBA2 was evaluated by MTT assay and it is expressed in % survival. Data are expressed as mean±SEM of 3 independent experiments (n=6). ANOVA one-way, Dunnett post hoc test. B) Western blot of cortical neurons under control conditions and relative quantification showing that SIMBA2 (0.25-0.5 μM) prevents the phosphorylation of APP at the T668 position in a dose-dependent manner. Data are expressed as mean±SEM of 3 independent experiments (n=6). ANOVA one-way, Dunnett's post-hoc test, ** p<0.01. C) Western blot and related quantification showing that SIMBA2 (0.25-0.5 μM) reduces P-c-Jun phosphorylation in neurons. Data are expressed as mean #SEM of 3 independent experiments (n=6). ANOVA one-way, Dunnett's post-hoc test. * p<0.05.

SIMBA2 was then tested, under control conditions, on mouse cortical neurons, where it showed no toxicity at 24 hours at the 3 doses tested (FIG. 4A). On the same neuronal model, SIMBA2 was shown to be able to significantly reduce the P-APP/APP (FIG. 4B) and P-c-Jun/c-Jun (FIG. 4C) ratios.

Figure 10:
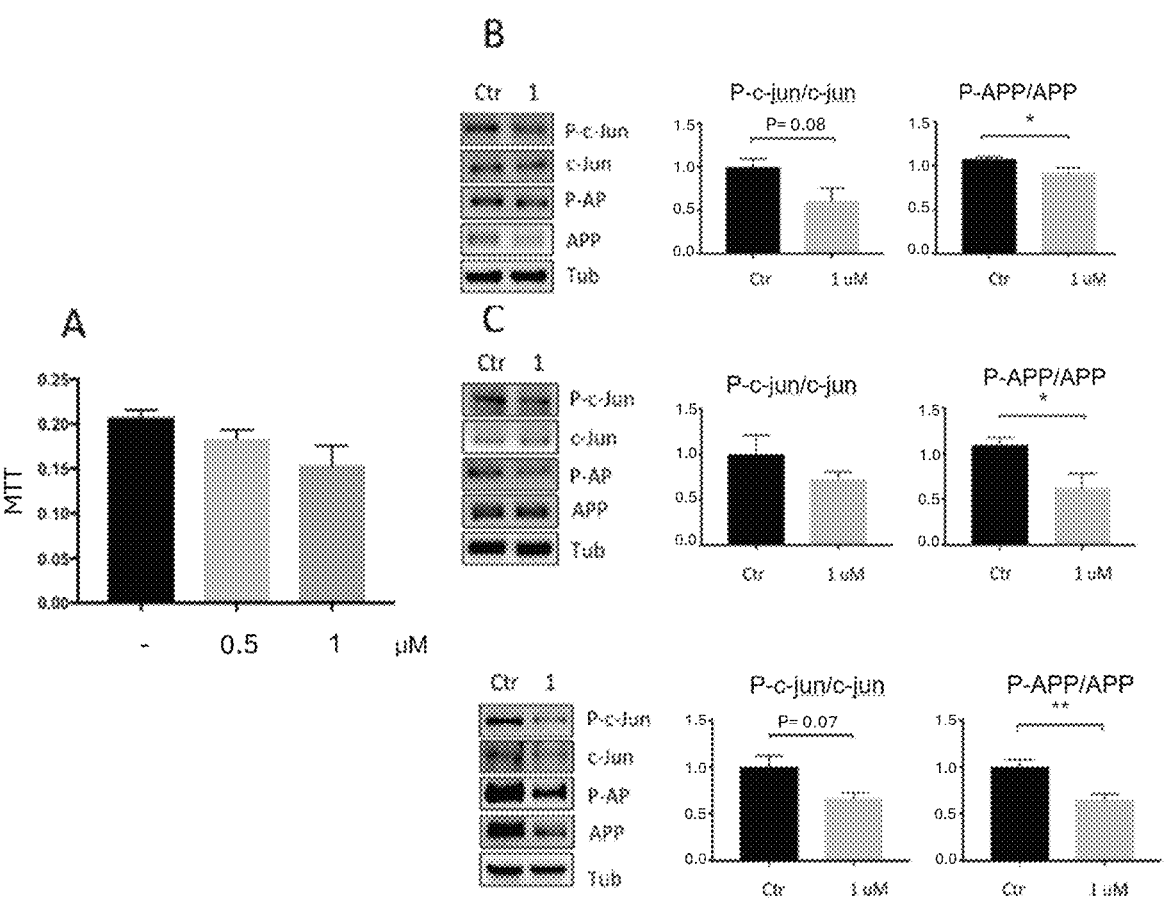
FIG. 10: A) Toxicity at the indicated concentrations of SIMBA2, evaluated by MTT assay and expressed as fold of change with respect to tcontrol. Data are expressed as mean±SEM of 3 independent experiments (n=6). ANOVA one-way, Dunnett post hoc test. B) Western blot of cortical neurons under control conditions in the absence (Ctr) or in the presence of SIMBA2 1 μM (1) and relative quantification showing that SIMBA2 (1 μM) at 24 h prevents the phosphorylation of P-c-Jun and reduces the phosphorylation of the APP at position T668 and C) the activity is maintained at 3 days and D) at 6 days after treatment. Data are expressed as mean±SEM of 2 independent experiments (n=5). ANOVA one-way. Dunnett's post-hoc test, * p<0.05 ** p<0.01.

SIMBA2, conjugated with the TAT protein synthesized in amino acids D, SEQ ID NO: 5, was then tested, under the same conditions as above, confirming non-toxicity at 24 hours at the two doses tested (FIG. 10A). On the same model, SIMBA2 conjugated with the TAT protein synthesized in amino acids D, tested at 1 μM, was confirmed to be able to significantly reduce the Pc-Jun/c-Jun and P-APP/APP ratios at 24 hours (FIG. 10B) and also at 3 days (FIG. 10C) and at 6 days (FIG. 10D).

Figure 5:
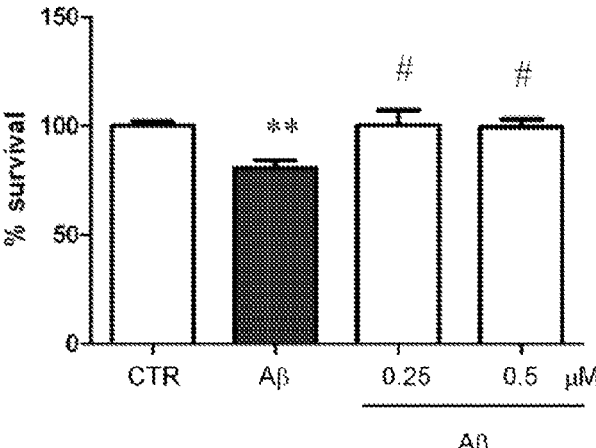
FIG. 5: MTT test showing how application of SIMBA2 (0.25-0.5 μM) 30 minutes before exposure to Aβ oligomers (1 μM for 24 hours) protects cortical neurons from death. Data are expressed as mean±SEM of 2 independent experiments (n=6). Two-way ANOVA, Tukey post-hoc test, ** p<0.01 vs CTR; #p<0.05 vs Aβ.

The protective effect of SIMBA2 against soluble Aβ oligomers, the most toxic species in AD, was subsequently examined. Neuronal death was verified by exposing neurons for 24 hours to 1 μM of Aβ oligomers, demonstrating a protective effect exerted by the SIMBA2 peptide, as shown by the data reported in FIG. 5 (black column: cells exposed to Aβ, white columns: negative control, or cells exposed to Aβ in the presence of the indicated doses of SIMBA2).

EXAMPLE 3: SIMBA2 ACTIVITY IN VIVO, AD MODEL, TGCRND8 MICE

The efficacy of SIMBA2 was at first tested in vitro against the toxicity of Aβ, the phosphorylation of c-Jun, as well as against the phosphorylation of APP and Tau. SIMBA2 was more efficient than D-JNKI1, as it completely eliminated Aβ toxicity in vitro at doses lower than the doses required by D-JNKI1. To define the dose to be used in vivo, a first acute treatment was performed, injecting animals with a single I.P. (intraperitoneal).

Old (9 months old) and symptomatic TgCRND8 mice were treated with two different doses of SIMBA2: a) 5.5 mg/kg and b) 22 mg/kg. This second dose is derived from the dose at which the D-JNKI1 CPP inhibitor was used in chronic (Sclip A. et al., 2011, cit., And Sclip A. et al., 2014 Cell Death Dis. 5: e1019).

To determine the effect of SIMBA2, its inhibitory effect on APP and Tau phosphorylation, the two main JNK targets in Alzheimer's disease in vivo, was measured.

Figure 6:
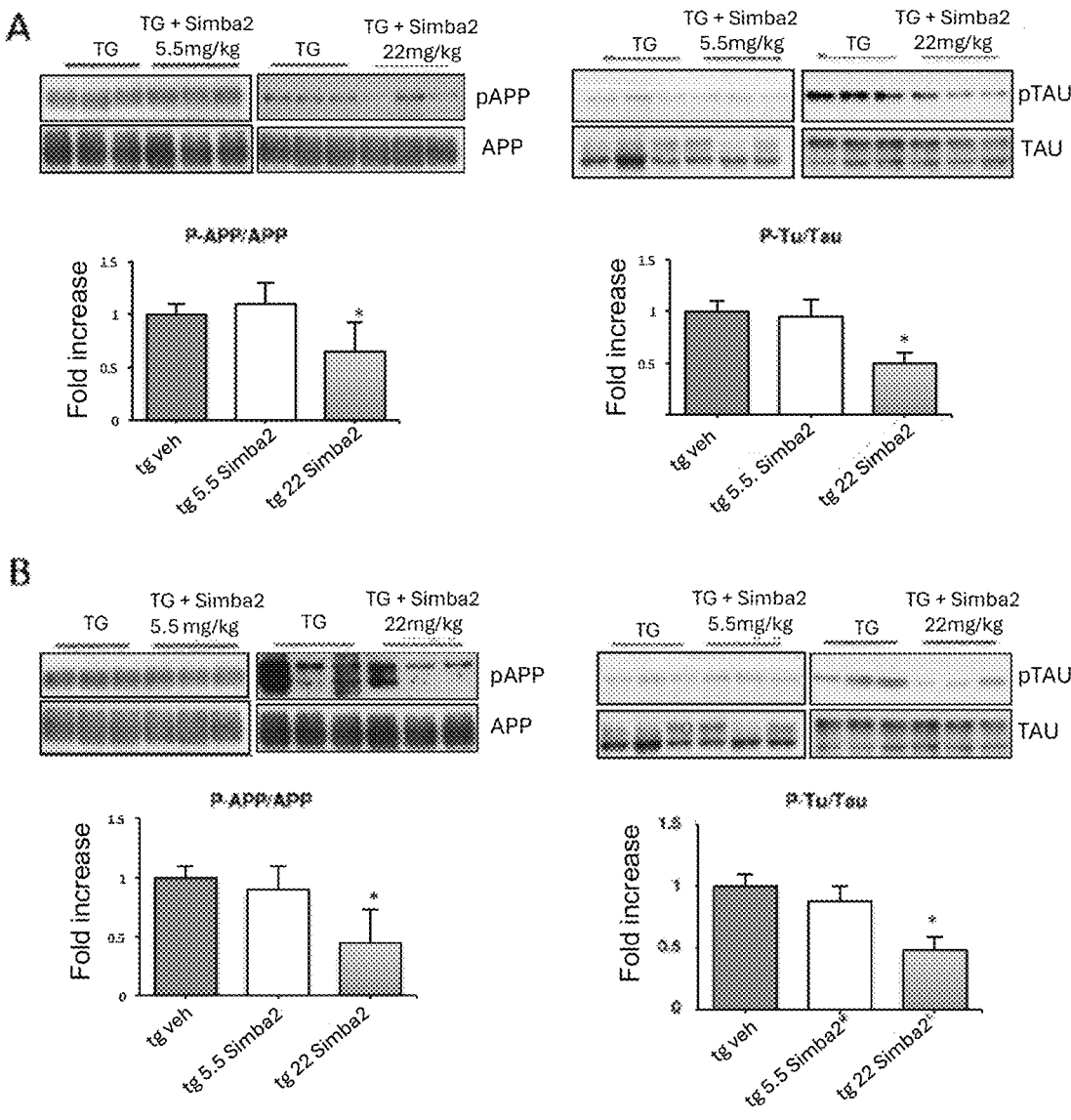
FIG. 6: SIMBA2 22 mg/kg prevents the phosphorylation of APP and Tau in the cortex (A) and hippocampus (B) homogenate of TgCRND8 mice. The Western Blot quantification data are expressed as mean±SEM.

A single injection of SIMBA2 5.5 mg/kg was unable to prevent APP and Tau phosphorylation, while the higher dose of 22 mg/kg was effective in reducing p-APP and p-Tau levels in the cortex (FIG. 6A) and hippocampus (FIG. 6B) of TgCRND8 mice.

The neuro protective effect of SIMBA2 was then studied against synaptopathy in vivo. Synaptic injury is the first neurodegenerative event in numerous brain pathologies and the development of therapies aimed at synaptic dysfunction is of fundamental importance. For this reason, the effect of SIMBA2 on synaptic dysfunction was examined by isolating postsynaptic density (PSD) with triton-insoluble fractionation (TIF).

At 9 months of age, symptomatic TgCRND8 mice treated with 5.5 mg/kg of SIMBA2 showed no significant differences in PSD composition compared to untreated mice, suggesting that the peptide was not effective. Indeed, TgCRND8 mice treated with vehicle or SIMBA2 5.5 mg/kg had similar levels of NMDA receptor subunit NR2A, NR2, GluR1 and GluR2 AMPA receptor subunit, PSD-95 protein and mature spine marker Drebrin (not shown).

Figure 7:
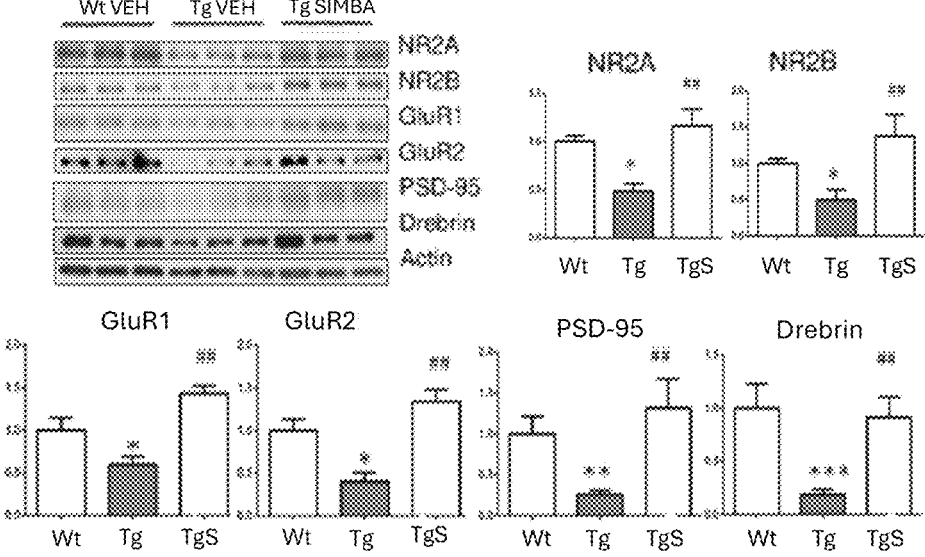
FIG. 7: Glutamate receptors in the post-synaptic region isolated with the Triton Insoluble Fractionation Protocol (TIF). In TgCRND8 mice, treatment with SIMBA2 (22 mg/kg) (TgS) rescues the oligomer-induced loss of Aβ of the NMDAR subunits (NR2A and NR2B), AMPAR (GluR1 and GluR2), PSD-95 and Drebrin, loss observed in the TgCRND8 (Tg) mice. The Western Blot quantification data are expressed as mean±SEM.

The same 9-month-old TgCRND8 mice subjected to a single injection of SIMBA2 at 22 mg/kg showed a significant increase in the biomarkers of the PSD active region in the postsynaptic element. Indeed, while the vehicle-treated TgCRND8 mice (black column in FIG. 7, Tg) showed a significant drop in the postsynaptic levels of NR2A, NR2B, GluR1, GluR2, PSD-95 and Drebrin, a single injection of SIMBA2 restored the decrease in the levels of the markers of the PSD region (white columns in FIG. 7, TgS). Therefore, SIMBA2 at the highest dose was able to prevent synaptopathy in vivo. Furthermore, in vivo treatment with SIMBA2 at a dose of 22 mg/kg did not lead to the onset of any noticeable side effects.

Figure 8:
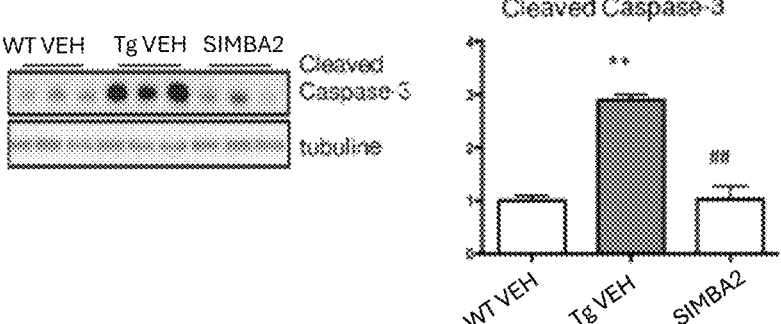
FIG. 8: Caspase-3 pathway in the postsynaptic compartment in TgCRND8 mice. Levels of cleaved caspase-3 in the TIF fraction of treated TgCRND8 mice were evaluated by Western Blot. Cleaved Caspase-3 increased 2.88-fold in TgCRND8 (TgVEH) mice compared with age-matched Wt (Wt VEH) mice. Treatment with SIMBA2 is able to restore the cleaved Caspase-3 levels to physiological ones (Student's t test, ** p<0.01, n=6).

The effect of SIMBA2 on caspase-3 cleavage was then tested. Caspase-3, the final effector of apoptotic death, is part of a metabolic pathway whose involvement in AD synaptopathy is widely demonstrated (D'Amelio M. et al. 2011 Nature Neuroscience 14:69-76; Sclip A. et al. 2013 Journal of Molecular Cell Biology 5, Issue 4:277-279). It was observed here that SIMBA2 blocks the activation of caspase-3, as shown in FIG. 8.

Figure 9:
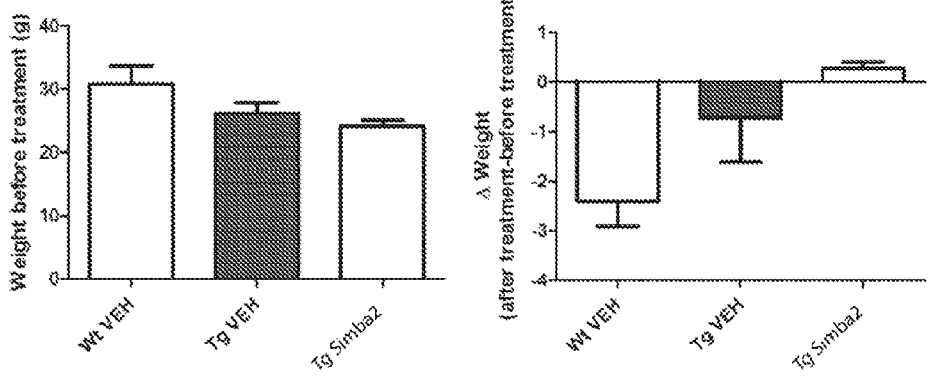
FIG. 9: A) Measurement of body weight in mice before treatment. Data are expressed as mean body weight (g)±SEM. B) Weight gain or loss was analyzed as the difference between the weight at the end and before the treatment. Data are expressed as mean±SEM.

The toxicity of SIMBA2 after a single injection was evaluated. As an index of the general health of the animals, the change in the body weight of the mice was evaluated. All groups showed comparable weight distribution before treatment (FIG. 9). 1 month after the I.P. injection, the body weight was measured again. As shown in FIG. 9B, the treated SIMBA2 mice did not show changes in body weight, suggesting the absence of side effects due to the treatment. Instead, a slight weight loss was observed in the Wt and Tg mice receiving the vehicle.

Finally, the protection obtained with SIMBA2 was quantified and compared with that obtained with D-JNKI1, a non-specific inhibitor of all JNK isoforms (Sclip et al., 2011, cit.) in an acute treatment on TgCRND8 mice. The yardstick was the change in the decrease in biomarker levels of the PSD region. The results are shown in Table 1.

TABLE 1

|  | SIMBA2 22 mg/kg | D-JNKI1 22 mg/kg |
|---|---|---|
| NR2A | 100 | 100 |
| NR2B | 100 | 100 |
| GluR1 | 100 | 100 |
| GluR2 | 100 | 48 |
| PSD-95 | 100 | 53 |
| Drebrin | 100 | 100 |

Treatment with SIMBA2 was shown to protect transgenic mice from loss of PSD proteins. SIMBA2 recovers 100% AMPA Glur2 and PSD-95 subunits more efficiently than D-JNKI1-treated mice. The results therefore highlight the greater efficacy of SIMBA2 compared to D-JNKI1 as well as the greater specificity. In particular, the data obtained on PSD-95 is relevant, where PSD-95 is an important constituent of the PSD region fraction and its accumulation, dispersion and degradation in the region are closely correlated with the alteration of the functionality and strength of the excitatory synapses.

SIMBA2, by blocking JNK3-mediated phosphorylation of PSD-95, stabilizes PSD-95 in the PSD region, inducing a normalization of NMDA and AMPA receptor levels in TgCRND8 AD symptomatic mice.

EXAMPLE 4: SIMBA2 ACTIVITY IN VIVO, AD MODEL, TG5XFAD MICE

The efficacy of SIMBA2 was tested on a second AD model, Tg5XFAD mice, in which the effect of SIMBA2 on synaptic dysfunction was examined by isolating the PSD with triton insoluble fractionation (TIF).

Figure 11:
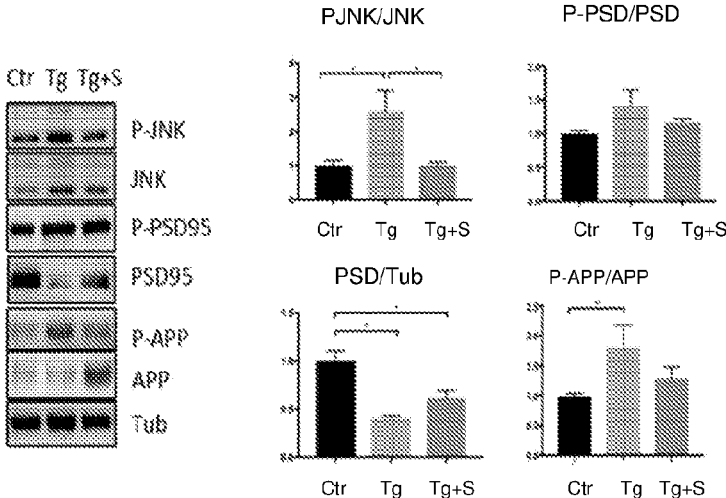
FIG. 11: In the post-synaptic region isolated with the triton-insoluble fractionation protocol (TIF), treatment with SIMBA2 (22 m/kg) in Tg5XFAD mice prevents JNK activation and APP phosphorylation. Western blot performed on the post-synaptic region TIF fraction from control mice (Ctr), from Tg5XFAD (Tg) mice and from Tg5XFAD mice treated with SIMBA2 (Tg+S), Western Blot quantification data are expressed as mean±SEM. ANOVA two-way, Tukey's post-hoc test. * p<0.05; ** p<0.01.

Pre-symptomatic 3-month-old Tg5XFAD mice, subjected to a single injection of SIMBA2 at 22 mg/kg, sacrificed 24 hours after administration, showed the prevention of increased JNK phosphorylation and APP phosphorylation. Indeed, while the vehicle-treated Tg5XFAD mice (FIG. 11, Tg column) showed a significant increase in JNK and APP phosphorylation compared to the control (FIG. 11. Ctr column), a single SIMBA2 injection restored levels of phosphorylation at the levels observed in the control (FIG. 11, Tg+S column).

Figure 12:
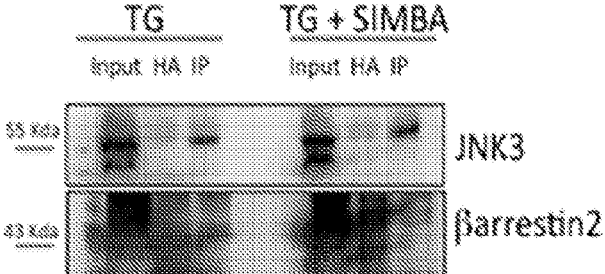
FIG. 12: SIMBA2 in Tg5XFAD mice prevents the interaction between JNK3 and β-arrestin-2. Co-Immunoprecipitation of JNK3-β-arrestin-2 in treated (TG+SIMBA) and untreated (TG) Tg5XFAD mice. Input=total lysate; HA=control; IP=immunoprecipitate.

In the same animal model, the ability of SIMBA2 to prevent the interaction between JNK3 and β-arrestin-2 was observed, as shown with an immunoprecipitation assay whose result in mice not treated or treated with a single 22 mg SIMBA2 dose/kg is shown in FIG. 12. Briefly, the total homogenate of one cerebral hemisphere was incubated overnight at 4° C. with 1 μg of anti-JNK3 or anti-HA antibodies. Dyna-beads (Thermo Fisher) were then incubated with the lysate for 1 hour at 4° C. The beads were washed five times with PBS1× and 0.5% Triton and the bound proteins were eluted with elution buffer (Thermo Fisher) and analyzed by western blotting.

EXAMPLE 5: SIMBA2 ACTIVITY IN VIVO, ACUTE TRAUMA

Figure 13:
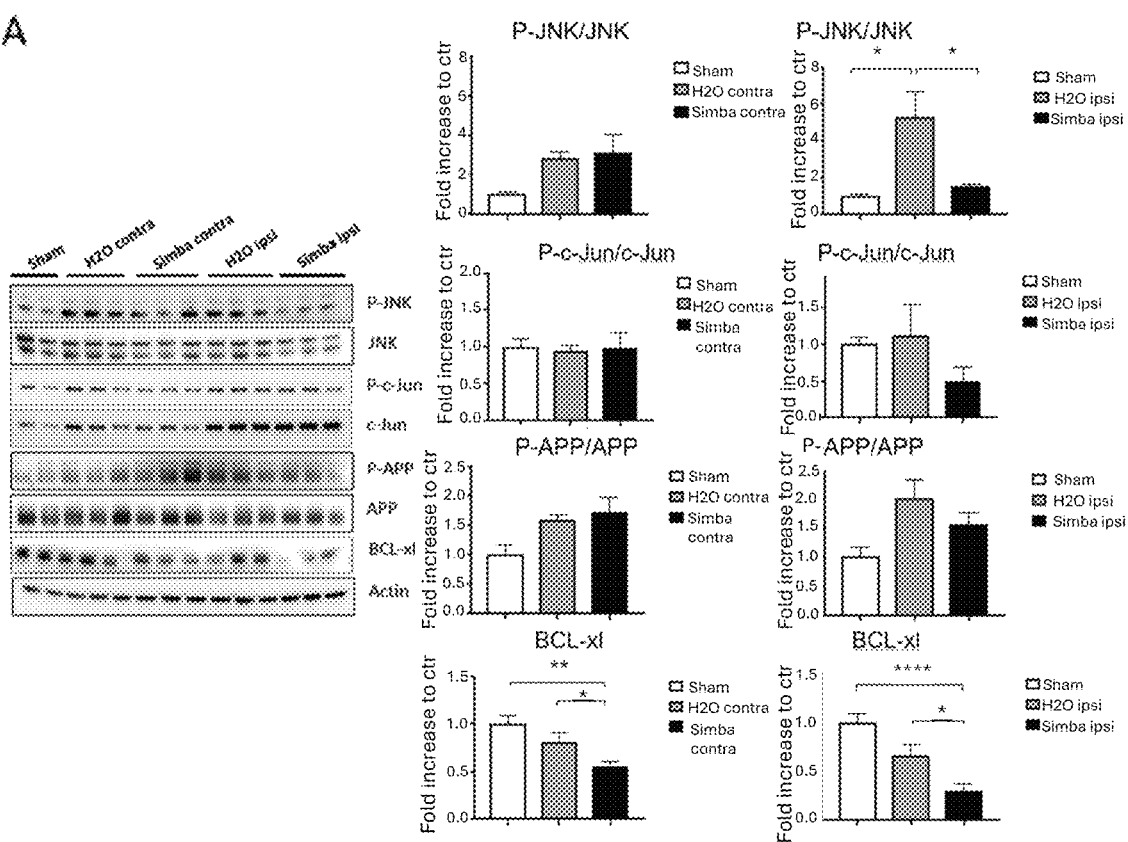
FIG. 13: Acute treatment, effect of SIMBA2 in the total homogenate of cortex (A) and in the isolated post-synaptic fraction with the triton-insoluble fractionation protocol (TIF) (B). The lysate was obtained from the contralateral (contra) or ipsilateral (ipsi) cortex with respect to the region of trauma. White column=sham; gray column=trauma, untreated; black column=trauma+SIMBA2. Data are expressed as mean±SEM, ANOVA two-ways. Tukey's post-hoc test, n=8. Significance towards control: * p<0.05;  p<0.01, ** p<0.0001.
Figure 13:
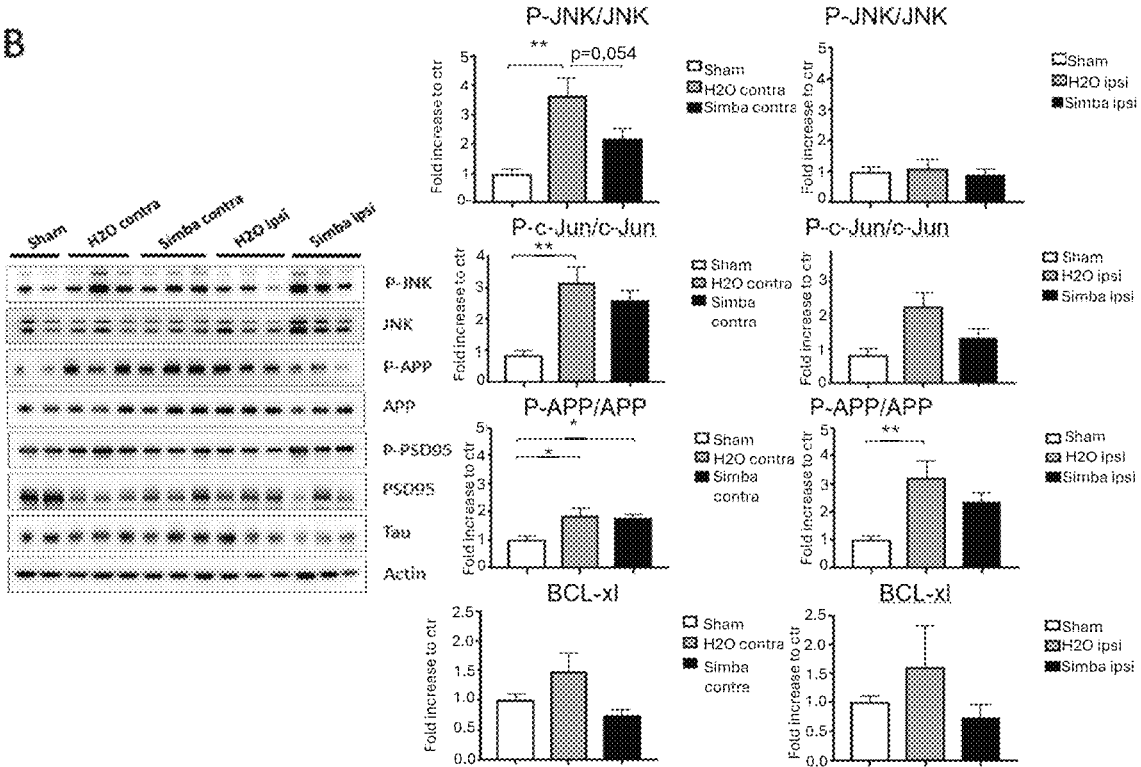

The well-established Traumatic Brain Injuri (TBI) model was selected as the acute treatment model. Briefly, the mice were anesthetized with inhalation of isoflurane then inserted into a stereotaxic apparatus. Brain injury was induced by a single unilateral controlled impact in the left parieto-temporal cortex (AP-2.5 mm, L-2.5 mm). During the impact, the piston acquires a speed of 5 m/s, a depth of 2 mm and a pause time of 0.1 s. During all surgical procedures, body temperature was maintained at 37° C. The sham mice received identical anaesthesia and surgery without brain injury. 10 minutes after the trauma, the mice were treated with 22 mg/kg of SIMBA2 and then sacrificed 48 hours after treatment. The contralateral and ipsilateral cortical regions with respect to the trauma were isolated. From these, total homogenate was obtained, FIG. 13A, and PSD fraction, FIG. 13B.

The data obtained in the total homogenate of the cortex show that, in the ipsilateral region, the trauma leads to an increase in the phosphorylation of JNK and APP. Treatment with SIMBA2 effectively counteracts the damage induced by trauma, supporting the effectiveness of SIMBA2 as a neuroprotective even in acute cases.

The data obtained in the TIF fraction show the effect of the damage in the contralateral region. The damage, in fact, starts from the postsynaptic region, so no changes are observed in the ipsilateral region since it has already been overcome. In this fraction, it is possible to observe how the treatment with SIMBA2 is able to restore the values observed in the animal not exposed to the trauma.

---

The invention claimed is:

1. A peptide, natural or synthetic, comprising an amino acid sequence that has at least 80% sequence identity with the sequence (SEQ ID NO: 1)
SDRSLHLEANEKGENVNVHVTKTRADKSKIKVSVRQYADINEKGEAQYK
CPVAQLE.

2. The peptide according to claim 1, which has at least 90% sequence identity with SEQ ID NO: 1.

3. The peptide according to claim 1, which has at least 95% sequence identity with SEQ ID NO: 1.

4. The peptide according to claim 1, which consists of SEQ ID NO: 1.

5. The peptide according to claim 1, which is conjugated to a polypeptide transport moiety.

6. The peptide according to claim 5, wherein said polypeptide transport moiety is TAT protein.

7. A pharmaceutical composition comprising at least one peptide according to claim 1 and a pharmaceutically acceptable carrier.

8. A method for treating an acute pathology of the nervous system of a subject, comprising administering an effective amount of a pharmaceutical composition comprising at least one peptide according to claim 6 and a pharmaceutically acceptable carrier to a subject in need thereof; wherein the acute pathology of the nervous system is selected from ischemia, traumatic brain injury, Alzheimer's, Parkinson's disease, Huntington's disease, frontotemporal dementia, Down syndrome, schizophrenia, spino-cerebellar ataxia, muscular atrophy, amyotrophic lateral sclerosis, progressive supranuclear palsy, corticobasal degeneration, Pick's disease, and prion diseases.

9. The method according to claim 8, wherein the acute pathology of the nervous system is Alzheimer's disease.

10. The method according to claim 8, wherein the acute pathology of the nervous system is traumatic brain injury.

\* \* \* \* \*

```
                    SEQUENCE LISTING

<160> NUMBER OF SEQ ID NOS: 5

<210> SEQ ID NO 1
<211> LENGTH: 56
<212> TYPE: PRT
<213> ORGANISM: Artificial Sequence
<220> FEATURE:
<223> OTHER INFORMATION: Designed peptide based on size and structure to
      act in the interaction among beta-arrestin-2 and JNK3

<400> SEQUENCE: 1

Ser Asp Arg Ser Leu His Leu Glu Ala Asn Glu Lys Gly Glu Asn Val
1               5                   10                  15

Asn Val His Val Thr Lys Thr Arg Ala Asp Lys Ser Lys Ile Lys Val
            20                  25                  30

Ser Val Arg Gln Tyr Ala Asp Ile Asn Glu Lys Gly Glu Ala Gln Tyr
        35                  40                  45

Lys Cys Pro Val Ala Gln Leu Glu
    50                  55

<210> SEQ ID NO 2
<211> LENGTH: 50
<212> TYPE: PRT
<213> ORGANISM: Artificial Sequence
<220> FEATURE:
<223> OTHER INFORMATION: Designed peptide based on size and structure to
      act in the interaction among beta-arrestin-2 and JNK3

<400> SEQUENCE: 2

Ser Asp Arg Ser Leu His Leu Glu Ala Glu Lys Gly Asn Val Asn Val
1               5                   10                  15

His Val Thr Lys Thr Glu Lys Gly Lys Ile Lys Val Ser Val Arg Gln
            20                  25                  30
```

-continued

```
Tyr Ala Asp Ile Glu Lys Gly Ala Gln Tyr Lys Cys Pro Val Ala Gln
        35                  40                  45

Leu Glu
    50

<210> SEQ ID NO 3
<211> LENGTH: 50
<212> TYPE: PRT
<213> ORGANISM: Artificial Sequence
<220> FEATURE:
<223> OTHER INFORMATION: Designed peptide based on size and structure to
      act in the interaction among beta-arrestin-2 and JNK3

<400> SEQUENCE: 3

Ser Asp Arg Ser Leu His Leu Glu Ala Glu Lys Gly Asn Val Asn Val
1               5                   10                  15

His Val Thr Lys Thr Ala Asp Lys Lys Ile Lys Val Ser Val Arg Gln
            20                  25                  30

Tyr Ala Asp Ile Glu Lys Gly Ala Gln Tyr Lys Cys Pro Val Ala Gln
        35                  40                  45

Leu Glu
    50

<210> SEQ ID NO 4
<211> LENGTH: 56
<212> TYPE: PRT
<213> ORGANISM: Artificial Sequence
<220> FEATURE:
<223> OTHER INFORMATION: Designed peptide based on size and structure to
      act in the interaction among beta-arrestin-2 and JNK3

<400> SEQUENCE: 4

Ser Asp Arg Ser Leu His Leu Glu Ala Asn Glu Lys Gly Glu Asn Val
1               5                   10                  15

Asn Val His Val Thr Lys Thr Asn Glu Lys Gly Glu Lys Ile Lys Val
            20                  25                  30

Ser Val Arg Gln Tyr Ala Asp Ile Asn Glu Lys Gly Glu Ala Gln Tyr
        35                  40                  45

Lys Cys Pro Val Ala Gln Leu Glu
    50                  55

<210> SEQ ID NO 5
<211> LENGTH: 11
<212> TYPE: PRT
<213> ORGANISM: Artificial Sequence
<220> FEATURE:
<223> OTHER INFORMATION: Protein TAT

<400> SEQUENCE: 5

Tyr Gly Arg Lys Lys Arg Arg Gln Arg Arg Arg
1               5                   10
```